United States Patent [19]
Tsutsumi et al.

[11] 3,954,658
[45] May 4, 1976

[54] OIL-IN-WATER EMULSION AND EMULSIFYING OR SOLUBILIZING COMPOSITION THEREFOR

[75] Inventors: Hisao Tsutsumi; Junichi Kawano; Ikuya Kinoshita; Hirokazu Nakayama; Toshino Ukena, all of Wakayama, Japan

[73] Assignee: Kao Soap Co., Ltd., Tokyo, Japan

[22] Filed: Aug. 5, 1975

[21] Appl. No.: 601,971

[30] Foreign Application Priority Data
Aug. 8, 1974  Japan.................................. 49-91086

[52] U.S. Cl. ................................ 252/312; 252/356; 424/59; 424/70
[51] Int. Cl.$^2$ ...................... B01J 13/00; B01F 17/34
[58] Field of Search ............................. 252/312, 356

[56] References Cited
UNITED STATES PATENTS

| | | | |
|---|---|---|---|
| 1,500,670 | 7/1924 | DeGroote ....................... | 252/312 X |
| 2,269,529 | 1/1942 | Goldsmith...................... | 252/312 X |
| 2,786,013 | 3/1957 | Behrens .......................... | 252/312 X |
| 3,634,285 | 1/1972 | Brooks............................. | 252/312 |
| 3,795,627 | 3/1974 | Langhans et al................. | 252/356 |

*Primary Examiner*—Richard D. Lovering
*Attorney, Agent, or Firm*—Woodhams, Blanchard and Flynn

[57] ABSTRACT

An emulsifying or solubilizing agent composition comprising 58 to 95% by weight of a surface active agent of the polyoxyethylene sorbitol-unsaturated fatty acid ester type having the formula

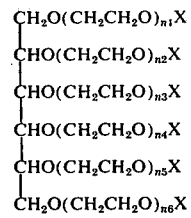

wherein the sum of $n1 + n2 + n3 + n4 + n5 + n6$ is from 10 to 60, and on the average, up to 3 of the X's are hydrogen and the balance of the X's are linear unsaturated acyl groups having 18 carbon atoms, 0.5 to 1.0% by weight of an alkali metal salt of a linear fatty acid having 12 to 18 carbon atoms, 2.5 to 6.0% by weight of a linear fatty acid, and 2 to 35% by weight of $C_{18}$ linear unsaturated fatty acid ester of a polyethylene glycol having an average molecular weight of 150 to 2,000.

10 Claims, No Drawings

OIL-IN-WATER EMULSION AND EMULSIFYING OR SOLUBILIZING COMPOSITION THEREFOR

BACKGROUND OF THE INVENTION

1. Field of the Invention

This invention relates to an emulsifying or solubilizing agent composition which is highly effective for emulsifying and solubilizing liquid vegetable oils and highly polar synthetic ester oils, the emulsification or solubilization of which has heretofore been regarded as being very difficult.

2. Description of the Prior Art

As emulsifiers for cosmetics, there have heretofore been used not only non-ionic surface active agents such as polyoxyethylene sorbitan-fatty acid esters, sorbitan-fatty acid esters, glycerol-fatty acid esters, polyethylene glycol-fatty acid esters and polyoxyethylenealkyl esters, but also a great variety of non-ionic, anionic, cationic and amphoteric surface active agents. In general, these emulsifiers have a good emulsifying activity to mineral oils composed of hydrocarbons and the like and animal oils such as squalane, and they provide stable emulsions of these oils. However, these surface active agents can scarcely emulsify liquid vegetable oils composed of triglycerides full of aliphatic hydrocarbon groups having unsaturated bonds (hereinafter referred to merely as "vegetable oils"), such as camellia oil and olive oil, or esters having at least one branched alkyl group, which are synthesized from a branched or linear higher fatty acid and a branched or linear higher alcohol (hereinafter referred to merely as "synthetic ester oils"), and stable emulsions of these vegetable oils or synthetic ester oils have not been provided.

SUMMARY OF THE INVENTION

We have discovered an emulsifying or solubilizing agent capable of readily emulsifying or solubilizing the aforesaid vegetable oils or synthetic ester oils to provide stable emulsions thereof. According to our invention, there is provided a composition formed by incorporating specific amounts of a fatty acid alkali metal salt, a fatty acid and an oleic acid ester of a polyethylene glycol into a polyoxyethylene sorbitol-fatty acid ester type surface active agent. More specifically, in accordance with this invention, there is provided an emulsifying or solubilizing agent composition comprising 58 to 95% by weight of a polyoxyethylene sorbitol-unsaturated fatty acid ester (hereinafter referred to as "component (I)") having the formula (A)

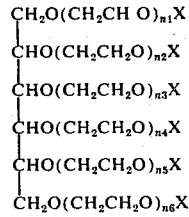

wherein the sum of $n1 + n2 + n3 + n4 + n5 + n6$ is from 10 to 60, and on the average up to 3 of the X's are hydrogen and the balance of the X's are linear unsaturated acyl groups having 18 carbon atoms, 0.5 to 1.0% by weight of an alkali metal salt of a linear saturated or olefinically unsaturated fatty acid having 12 to 18 carbon atoms (hereinafter referred to as "component (II)"), 2.5 to 6.0% by weight of a linear saturated or olefinically unsaturated fatty acid having 12 to 18 carbon atoms (hereinafter referred to as "component (III)"), and 2 to 35% by weight of a $C_{18}$ linear unsaturated fatty acid ester of a polyethylene glycol having an average molecular weight of 150 to 2,000 (hereinafter referred to as "component (IV)").

When the above composition is used as an emulsifying or solubilizing agent, the aforesaid types of vegetable oils and synthetic ester oils, which are highly polar emollient oils and have heretofore been regarded as being difficult to emulsify, can easily be emulsified or solubilized, and good, stable and ideal emulsions of these oils can be obtained. These vegetable oils are liquid vegetable oils composed of triglycerides containing many unsaturated aliphatic hydrocarbon groups, such as camellia oil, olive oil, safflower oil, rapeseed oil, palm oil and cotton seed oil, and the synthetic ester oils are esters having at least one branched alkyl group, which are synthesized from branched or linear higher fatty acids and branched or linear higher alcohols. As such synthetic ester oil, there can be mentioned, for example, 2-heptylundecyl isostearate, glyceroltris-2-ethylhexanoate, hexadecyl-2-ethylhexanoate, hexadecyl isostearate and hexadecyl isotridecanoate. These vegetable oils and synthetic ester oils are especially useful for cosmetics, and by the use of the composition of this invention, it is possible to employ these oils in the emulsified or solubilized state in cosmetics. More specifically, it is possible to incorporate such emulsified or solubilized vegetable oils or synthetic ester oils into various cosmetic creams and lotions such as sun creams and hair creams, and to obtain cosmetics which are superior to conventional cosmetics composed mainly of mineral oils, with respect to their mild emollient effects. The composition of this invention exhibits an excellent emulsifying effect not only to these vegetable oils and synthetic ester oils, but also to mineral oils and animal oils which can also be emulsified by conventional emulsifiers.

As will be seen from the above formula (A), the polyoxyethylene sorbitol-unsaturated fatty acid ester used as the component (I) in this invention is obtained by partially or fully esterifying a sorbitol-ethylene oxide adduct with an unsaturated fatty acid having 18 carbon atoms, such as oleic acid. Among the 6 hydroxyl groups of said adduct, from 3 to 6 of such groups, on the average, are esterified. In other words, in the formula (A), from 3 to 6 of the X's are acyl groups and the remaining X's are hydrogen. (Hereinafter, the number of such acyl groups is referred to as "the degree of esterification".) When a compound having a lower degree of esterification outside the above range is employed, the emulsifying effect is diminished and good emulsions cannot be obtained. Further, the stability is reduced. Unsaturated fatty acids having 18 carbon atoms, preferably oleic acid and linoleic acid, are employed for this esterification. Thus, from 3 to 6 of the X's of the Formula (A) compound have the formula RCO—, wherein R is an olefinically unsaturated acyclic unbranched hydrocarbon radical having 17 carbon atoms and having from one to 4 double bonds in the hydrocarbon chain. If saturated fatty acids such as stearic acid and palmitic acid are employed for esterifying the sorbitolethylene oxide adduct, the emulsifying effect of compositions containing such esters is very low. Further, since esters of such saturated fatty acids are solid at room temperature, the use of such saturated fatty acids for esterification purposes is not acceptable. The compound of formula (A) is synthesized by customary methods by dissolving sorbitol in a solvent such as xylene, adding thereto ethylene oxide in the presence of a basic catalyst to cause an addition reaction between sorbitol and ethylene oxide, adding to that adduct an unsaturated fatty acid in an amount of from 3 to 6 moles per mole of the resulting adduct, carrying out esterification at 220° to 240°C and decolorizing and purifying the final reaction product.

It is critial that the composition of this invention consists essentially of 58 to 95% by weight of the component (I), 0.5 to 1.0% by weight of the component (II), 2.5 to 6.0% by weight of the component (III) and 2 to 35% by weight of the component (IV). Compositions outside this range do not have a satisfactory emulsifying or solubilizing effect to the aforesaid vegetable oils and synthetic ester oils, and because of the poor stability of any emulsion that may be formed, the resulting emulsions are destroyed in a short time when they are allowed to stand still, resulting in phase separation.

In view of the properties of the oils to which the composition of this invention is applied, the emulsifying or solubilizing agent composition of this invention is especially valuable when used for cosmetics, but it can be utilized as an emulsifier or solubilizing agent in various fields where these oils are employed, namely in the arts of foodstuffs, fiber-treating oils, detergents, metal-processing oils and the like. In general, the composition of this invention is employed in an amount of from 5 to 100 percent by weight, based on the weight of the oil component, to form oil-in-water emulsions.

This invention will now be further described in detail by reference to the following illustrative Examples. In the following examples, all references to "%" and "parts" are by weight, unless otherwise indicated.

EXAMPLE 1

Tests of the emulsification of various oils were conducted by using emulsifiers having the following compositions:

| Ingredient | Compositon (%) of Emulsifier | | |
|---|---|---|---|
| | a | b | c |
| Component (I)* | 60.0 | 70.0 | 80.0 |
| Component (II) (sodium oleate) | 0.7 | 0.7 | 0.7 |
| Component (III) (oleic acid) | 5.0 | 5.0 | 5.0 |
| Component (IV) (average molecular weight = 600) | 34.3 | 24.3 | 14.3 |

*As the component (I), there were employed 7 kinds of compounds differing in the degree of esterification, ranging from a compound in which the degree of esterification with oleic acid was 0 to a compound in which 6 hydroxyl groups were completely esterified. In each of these compounds the average mole number of the added ethylene oxide was 30.

Test Procedures

A mixture of 20 parts of the oil component, 5 parts of the emulsifying agent composition and 75 parts of deionized water was emulsified at a temperature of 70°C, employing an agitating propeller rotation rate of 600 rpm, according to the phase inversion emulsification method. The emulsifiability and stability of each emulsion were evaluated based on the following standards:

1. Emulsifiability:

The state of the as-prepared emulsion was examined and observed with the naked eye and by a microscope, and the emulsifiability was evaluated by the following rating scale:

A: bluish white emulsion of fine particles, the average particle size as measured by using the microscope being smaller than 1 $\mu$ B: milky white emulsion, the average particle size as measured by using the microscope being 1 to 5 $\mu$ C: opaque crude emulsion, the average particle size as measured by using the microscope being larger than 5 $\mu$ In general, the invention provides mostly A grade emulsions, but some acceptable B grade emulsions can be obtained also.

2. Stability:

The emulsion comprising 75 parts of the aqueous phase and 25 parts of the oil phase was allowed to stand still at 25°C for 7 days, and the ratios of separation of the emulsion into oil and aqueous phases were determined. The stability was calculated from these separation ratios according to the following formula:

Stability Point = (Ratio (vol %) of Separation of Oil Phase + Ratio (vol %) of Separation of aqueous phase) × 1/10

For example, an emulsion which retains a completely emulsified state (no phase separation) has a stability point of 0 (zero) and an emulsion which has been separated completely into an oil phase and an aqueous phase has a stability point of 20. Thus, the lowere the stability point, the better is the emulsion.

The results are shown in Table 1.

Table 1

| Emulsifier Composition | Oil | Emulsifiability Stability | (Degree of Esterification in Component (I)) (number of acyl groups in formula (A)) | | | | | | |
|---|---|---|---|---|---|---|---|---|---|
| | | | 0 | 1 | 2 | 3 | 4 | 5 | 6 |
| a | Olive Oil | Emulsifiability | C | C | B | A | A | A | B |
| | | Stability | 20.0 | 15.0 | 12.0 | 0.0 | 0.0 | 0.0 | 2.5 |
| | Camellia Oil | Emulsifiability | C | C | B | A | A | A | B |
| | | Stability | 20.0 | 15.7 | 9.7 | 0.0 | 0.0 | 0.0 | 2.5 |
| | 2-Heptylundecyl Isostearate | Emulsifiability | C | C | B | A | A | A | A |
| | | Stability | 18.3 | 15.3 | 4.3 | 0.0 | 0.0 | 0.0 | 0.0 |
| b | Olive Oil | Emulsifiability | C | C | C | B | A | A | B |
| | | Stability | 20.0 | 15.0 | 12.5 | 4.3 | 0.0 | 0.0 | 2.5 |
| | Camellia Oil | Emulsifiability | C | C | C | A | A | A | A |
| | | Stability | 20.0 | 15.3 | 10.8 | 0.0 | 0.0 | 0.0 | 0.0 |
| | 2-Heptylundecyl Isostearate | Emulsifiability | C | C | C | A | A | A | A |
| | | Stability | 20.0 | 17.8 | 4.5 | 0.0 | 0.0 | 0.0 | 0.0 |
| c | Olive Oil | Emulsifiability | C | C | C | B | A | A | A |
| | | Stability | 20.0 | 20.0 | 15.7 | 10.0 | 0.0 | 0.0 | 0.0 |
| | Camellia Oil | Emulsifiability | C | C | C | A | A | A | A |
| | | Stability | 20.0 | 18.7 | 13.0 | 0.0 | 0.0 | 0.0 | 0.0 |
| | 2-Heptylundecyl | Emulsifiability | C | C | C | A | A | A | A |

Table 1-continued

| Emulsifier Composition | Oil | Emulsifiability Stability | (Degree of Esterification in Component (I)) (number of acyl groups in formula (A)) | | | | | | |
|---|---|---|---|---|---|---|---|---|---|
| | Isostearate | Stability | 20.0 | 19.5 | 8.3 | 0.0 | 0.0 | 0.0 | 0.0 |

As is seen from the above results, in the composition of this invention, when the average degree of esterification of the component (I) (the number of acyl groups as X in the formula (A)) is within the range of from 3 to 6, an excellent emulsifying effect is attained and an emulsion of good stability is obtained. On the other hand, when the average degree of esterification is 2 or lower, the emulsifying effect is low, and the stability of the resulting emulsion is bad and significant phase separation occurs.

EXAMPLE 2

(Emulsification of Camellia Oil)

Tests of the emulsification of camellia oil were conducted by using various emulsifiers (compositions) as shown in Table 2. The compounding proportions were 20 parts of camellia oil, 5 parts of emulsifier composition and 75 parts of deionized water. The test methods and evaluation methods were the same as described in Example 1 except that the stability was determined after the passage of 1 day and 1 week, respectively, and the emulsion was allowed to stand at 5°, 20° or 40°C.

The results are shown in Table 2.

EXAMPLE 3

(Emulsification of Olive Oil)

In the same manner as described in Example 2, emulsification tests were conducted by using a mixture of 20 parts of olive oil, 5 parts of an emulsifier (composition) and 75 parts of deionized water.

The results are shown in Table 3.

EXAMPLE 4

(Emulsification of 2-Heptylundecyl Isostearate)

In the same manner as described in Example 2, the emulsification tests were conducted by using a mixture of 20 parts of a synthetic ester oil obtained by esterification of 2-heptylundecanol with isostearic acid, 5 parts of an emulsifier (composition) and 75 parts of deionized water. The results are shown in Table 4.

EXAMPLE 5

(Emulsification of Glycerol Tris-2-ethylhexanoate)

In the same manner as described in Example 2, the emulsification tests were conducted by using a mixture of 20 parts of the above synthetic ester oil, 5 parts of an emulsifier (composition) and 74 parts of deionized water. The results are shown in Table 5.

In each of the following Tables 2–5, the emulsifier products of the invention tested had the following characteristics:

| Products of the Invention | $n1+n2+n3+n4+n5+n6$ | Degree of Esterification of (I) | II | III | Average Molecular Weight of (IV) |
|---|---|---|---|---|---|
| 1-1 | 10 | 3.0 | sodium laurate | lauric acid | 163 |
| 1-2 | 20 | 4.0 | sodium laurate | lauric acid | 313 |
| 1-3 | 30 | 4.5 | sodium oleate | oleic acid | 458 |
| 1-4 | 30 | 4.5 | sodium laurate | myristic acid | 458 |
| 1-5 | 40 | 4.5 | sodium myristate | myristic acid | 603 |
| 1-6 | 60 | 5.0 | sodium oleate | oleic acid | 898 |

In the comparative products 2-1 to 2-8, the degree of esterification of component (I) was 4.5, the component (II) was sodium oleate, the component (III) was oleic acid and the average molecular weight of component (IV) was 600. It will be noted that in comparative products 2-1 to 2-8, the proportions of the ingredients are outside the ranges of proportions of the ingredients according to the invention.

Comparative products 3-1 to 3-7, 4-1 to 4-5, 5-1 to 5-6, 6, 7-1 and 7-2 consisted of the components as listed in the Tables.

In the Tables, the mark (*) indicates that the emulsifiability was low, although because the viscosity of the emulsion was so high that no phase separation occurred.

Table 2

| | Results of Tests of Emulsification of Camellia Oil | | | | | |
|---|---|---|---|---|---|---|
| Invention Emulsifiers | Composition Proportion (wt.%) | | | | HLB | Emulsion Type |
| | (I) | (II) | (III) | (IV) | | |
| 1-1 | 73.5 | 0.72 | 4.8 | 20.98 | 8.2 | O/W |
| 1-2 | 85.0 | 0.65 | 4.5 | 9.85 | 9.2 | O/W |
| 1-3 | 72.0 | 0.90 | 3.7 | 23.40 | 10.6 | O/W |
| 1-4 | 70.0 | 0.70 | 4.2 | 25.10 | 10.3 | O/W |
| 1-5 | 60.5 | 0.92 | 4.4 | 34.18 | 11.6 | O/W |
| 1-6 | 75.0 | 0.58 | 3.7 | 20.72 | 13.2 | O/W |
| Comparative Emulsifiers | | | | | | |
| 2-1 | 70.0 | 0 | 5.0 | 25.0 | 10.3 | O/W |
| 2-2 | 69.8 | 0.2 | 0 | 30.0 | 10.3 | O/W |
| 2-3 | 72.0 | 0.2 | 1.4 | 26.4 | 10.3 | O/W |
| 2-4 | 40.2 | 0.6 | 4.2 | 55.0 | 10.1 | O/W |
| 2-5 | 20.0 | 0.6 | 2.4 | 77.0 | 10.0 | O/W |
| 2-6 | 100.0 | 0 | 0 | 0 | 10.4 | O/W |
| 2-7 | 0 | 0 | 0 | 100 | 9.9 | O/W |
| 2-8 | 0 | 0 | 100 | 0 | — | O/W |
| 3-1 | POE (20) sorbitan mono- | | | | 8.0 | O/W |
| 3-2 | oleate/sorbitan | | | | 9.0 | O/W |

Table 2-continued

Results of Tests of Emulsification of Camellia Oil

| Invention Emulsifiers | Composition Proportion (wt.%) | | | | HLB | Emulsion Type |
|---|---|---|---|---|---|---|
| | (I) | (II) | (III) | (IV) | | |
| 3-3 | monooleate | | | | 10.0 | O/W |
| 3-4 | | | | | 11.0 | O/W |
| 3-5 | | | | | 12.0 | O/W |
| 3-6 | | | | | 13.0 | O/W |
| 3-7 | POE (20) sorbitan trioleate | | | | 11.0 | O/W |
| 4-1 | POE (8) stearate/glycerol monostearate | | | | 8.0 | O/W |
| 4-2 | | | | | 9.0 | O/W |
| 4-3 | | | | | 10.0 | O/W |
| 4-4 | | | | | 11.0 | O/W |
| 4-5 | POE (50) stearate/glycerol monostearate | | | | 12.0 | O/W |
| 4-6 | ″ | | | | 13.0 | O/W |
| 5-1 | POE (5) oleyl ether | | | | 8.8 | O/W |
| 5-2 | POE (5) nonylphenyl ether | | | | 9.2 | O/W |
| 5-3 | POE (6) oleyl ether | | | | 10.0 | O/W |
| 5-4 | POE (6) stearyl ether | | | | 9.4 | O/W |
| 5-5 | POE (7) cetyl ether | | | | 10.7 | O/W |
| 5-6 | POE (9) oleyl ether | | | | 12.1 | O/W |
| 6 | polyoxyethylene-polyoxypropylene condensate | | | | — | O/W |
| 7-1 | sodium oleate | | | | — | O/W |
| 7-2 | potassium stearate | | | | — | O/W |

| Invention Emulsifiers | Emulsifiability | Stability of Formed Emulsion | | | | | |
|---|---|---|---|---|---|---|---|
| | | after one day's standing | | | after one week's standing | | |
| | | 5°C | 20°C | 40°C | 5°C | 20°C | 40°C |
| 1-1 | A | 0 | 0 | 0 | 0 | 0 | 0 |
| 1-2 | A | 0 | 0 | 0 | 0 | 0 | 0 |
| 1-3 | A | 0 | 0 | 0 | 0 | 0 | 0 |
| 1-4 | A | 0 | 0 | 0 | 0 | 0 | 0 |
| 1-5 | A | 0 | 0 | 0 | 0 | 0 | 0 |
| 1-6 | B | 0 | 0 | 0 | 4.5 | 5.2 | 5.2 |
| Comparative Emulsifiers | | | | | | | |
| 2-1 | C | 2.5 | 2.5 | 3.5 | 9.3 | 9.7 | 10.0 |
| 2-2 | B | 0.2 | 0.5 | 0.5 | 12.5 | 12.5 | 12.5 |
| 2-3 | A | 0 | 0 | 0 | 8.0 | 8.0 | 8.3 |
| 2-4 | C | 9.7 | 9.5 | 9.7 | 12.5 | 12.5 | 12.5 |
| 2-5 | C | 8.0 | 8.5 | 8.5 | 10.0 | 9.7 | 10.0 |
| 2-6 | C | 12.3 | 12.7 | 15.0 | 18.5 | 18.5 | 18.5 |
| 2-7 | C | 8.5 | 10.0 | 12.5 | 10.0 | 12.5 | 13.4 |
| 2-8 | C | 20.0 | 20.0 | 20.0 | 20.0 | 20.0 | 20.0 |
| 3-1 | C | 8.5 | 8.5 | 8.5 | 8.7 | 8.7 | 9.3 |
| 3-2 | C | 8.0 | 8.0 | 8.5 | 8.0 | 8.0 | 8.7 |
| 3-3 | C | 8.5 | 8.5 | 8.7 | 9.3 | 9.3 | 9.3 |
| 3-4 | C | 8.7 | 8.7 | 8.7 | 9.3 | 9.3 | 9.3 |
| 3-5 | C | 9.3 | 9.3 | 9.3 | 9.7 | 9.8 | 14.6 |
| 3-6 | C | 9.3 | 9.3 | 9.3 | 9.5 | 9.7 | 14.9 |
| 3-7 | C | 8.0 | 8.0 | 8.5 | 8.7 | 9.3 | 9.3 |
| 4-1 | C | 0* | 0* | 0* | 0* | 0* | 0* |
| 4-2 | C | 0* | 0* | 0* | 0* | 0* | 0* |
| 4-3 | C | 0* | 0* | 2.5 | 0* | 0* | 5.3 |
| 4-4 | C | 0* | 0* | 8.0 | 0* | 0* | 9.3 |
| 4-5 | C | 0* | 5.3 | 8.0 | 0* | 8.7 | 8.0 |
| 4-6 | C | 0* | 8.0 | 8.8 | 0* | 8.7 | 9.1 |
| 5-1 | C | 12.5 | 12.5 | 15.0 | 12.5 | 15.0 | 15.0 |
| 5-2 | C | 17.0 | 17.5 | 18.5 | 20.0 | 20.0 | 20.0 |
| 5-3 | C | 8.0 | 8.7 | 8.7 | 8.0 | 9.3 | 9.3 |
| 5-4 | C | 8.0 | 8.7 | 8.7 | 8.0 | 9.3 | 9.3 |
| 5-5 | C | 6.6 | 7.3 | 10.0 | 6.7 | 7.3 | 10.0 |
| 5-6 | C | 10.0 | 17.5 | 19.5 | 10.0 | 18.0 | 20.0 |
| 6 | C | 9.3 | 9.3 | 9.3 | 17.5 | 12.5 | 9.3 |
| 7-1 | B | 5.2 | 5.7 | 5.7 | 9.3 | 9.7 | 9.7 |
| 7-2 | B | 5.0 | 5.7 | 5.7 | 10.0 | 8.5 | 10.0 |

Table 3

Results of Tests of Emulsification of Olive Oil

| Invention Emulsifiers | Composition Proportion (wt.%) | | | | HLB | Emulsion Type |
|---|---|---|---|---|---|---|
| | (I) | (II) | (III) | (IV) | | |
| 1-2 | 85.0 | 0.65 | 4.5 | 9.85 | 9.2 | O/W |
| 1-3 | 72.0 | 0.90 | 3.7 | 23.40 | 10.6 | O/W |
| 1-4 | 70.0 | 0.70 | 4.2 | 25.10 | 10.3 | O/W |
| 1-5 | 60.5 | 0.92 | 4.4 | 34.18 | 11.6 | O/W |
| Comparative Emulsifiers | | | | | | |
| 2-1 | 70.0 | 0 | 5.0 | 25.0 | 10.3 | O/W |
| 2-2 | 69.8 | 0.2 | 0 | 30.0 | 10.3 | O/W |
| 2-3 | 72.0 | 0.2 | 1.4 | 26.4 | 10.3 | O/W |
| 2-4 | 40.2 | 0.6 | 4.2 | 55.0 | 10.1 | O/W |

Table 3-continued

Results of Tests of Emulsification of Olive Oil

| Invention Emulsifiers | (I) | Composition Proportion (wt.%) (II) | (III) | (IV) | HLB | Emulsion Type |
|---|---|---|---|---|---|---|
| 2-5 | 20.0 | 0.6 | 2.4 | 77.0 | 10.0 | O/W |
| 2-6 | 100.0 | 0 | 0 | 0 | 10.4 | O/W |
| 2-7 | 0 | 0 | 0 | 100 | 9.9 | O/W |
| 2-8 | 0 | 0 | 100 | 0 | — | O/W |
| 3-1 | | POE (20) sorbitan mono- | | | 8.0 | O/W |
| 3-2 | | oleate/sorbitan | | | 9.0 | O/W |
| 3-3 | | monooleate | | | 10.0 | O/W |
| 3-4 | | | | | 11.0 | O/W |
| 3-5 | | | | | 12.0 | O/W |
| 3-6 | | | | | 13.0 | O/W |
| 3-7 | | POE (20) sorbitan trioleate | | | 11.0 | O/W |
| 4-1 | | POE (8) stearate/glycerol | | | 8.0 | O/W |
| 4-2 | | monostearate | | | 9.0 | O/W |
| 4-3 | | | | | 10.0 | O/W |
| 4-4 | | | | | 11.0 | O/W |
| 4-5 | | POE (50) stearate/glycerol monostearate | | | 12.0 | O/W |
| 4-6 | | '' | | | 13.0 | O/W |
| 5-1 | | POE (5) oleyl ether | | | 8.8 | O/W |
| 5-2 | | POE (5) nonylphenyl ether | | | 9.2 | O/W |
| 5-3 | | POE (6) oleyl ether | | | 10.0 | O/W |
| 5-4 | | cetyl (6) stearyl ether | | | 9.4 | O/W |
| 5-5 | | POE (7) cetyl ether | | | 10.7 | O/W |
| 5-6 | | POE (9) oleyl ether | | | 12.1 | O/W |
| 6 | | polyoxyethylene-polyoxypropylene condensate | | | — | O/W |
| 7-1 | | sodium oleate | | | — | O/W |
| 7-2 | | potassium oleate | | | — | O/W |

| Invention Emulsifiers | Emulsifiability | Stability of Formed Emulsion after one day's standing | | | after one week's standing | | |
|---|---|---|---|---|---|---|---|
| | | 5°C | 20°C | 40°C | 5°C | 20°C | 40°C |
| 1-2 | B | 0 | 0 | 0 | 0 | 0 | 0 |
| 1-3 | A | 0 | 0 | 0 | 0 | 0 | 0 |
| 1-4 | A | 0 | 0 | 0 | 0 | 0 | 0 |
| 1-5 | A | 0 | 0 | 0 | 0 | 0 | 0 |
| Comparative Emulsifiers | | | | | | | |
| 2-1 | C | 9.5 | 9.7 | 9.7 | 15.0 | 15.0 | 15.0 |
| 2-2 | B | 2.5 | 2.7 | 3.2 | 10.0 | 10.0 | 10.0 |
| 2-3 | B | 0.2 | 0.2 | 3.0 | 10.0 | 10.0 | 10.0 |
| 2-4 | C | 7.3 | 9.5 | 9.5 | 9.3 | 9.5 | 10.0 |
| 2-5 | C | 9.5 | 9.5 | 9.5 | 9.7 | 10.0 | 13.0 |
| 2-6 | C | 9.5 | 9.5 | 9.5 | 15.0 | 15.0 | 15.0 |
| 2-7 | C | 10.0 | 10.0 | 15.0 | 15.0 | 15.0 | 15.0 |
| 2-8 | C | 20.0 | 20.0 | 20.0 | 20.0 | 20.0 | 20.0 |
| 3-1 | C | 9.0 | 9.0 | 9.0 | 9.3 | 9.3 | 9.3 |
| 3-2 | C | 9.5 | 9.5 | 9.5 | 9.5 | 9.5 | 10.0 |
| 3-3 | C | 9.5 | 9.5 | 10.0 | 9.7 | 10.0 | 10.0 |
| 3-4 | C | 9.5 | 9.5 | 10.0 | 10.0 | 10.0 | 10.0 |
| 3-5 | C | 8.5 | 9.5 | 9.5 | 9.5 | 10.0 | 10.0 |
| 3-6 | C | 10.0 | 9.5 | 9.5 | 10.0 | 9.5 | 10.3 |
| 3-7 | C | 10.0 | 10.0 | 12.5 | 10.0 | 10.0 | 15.0 |
| 4-1 | C | 0* | 0* | 0* | 0* | 0* | 0* |
| 4-2 | C | 0* | 0* | 0* | 0* | 0* | 0* |
| 4-3 | C | 0* | 0* | 0* | 0* | 0* | 0* |
| 4-4 | C | 0* | 0.6 | 8.0 | 0* | 0.6 | 8.0 |
| 4-5 | C | 0* | 1.0 | 8.0 | 0* | 8.3 | 8.0 |
| 4-6 | C | 0* | 1.0 | 9.5 | 0* | 8.7 | 9.5 |
| 5-1 | C | 8.0 | 8.7 | 9.5 | 8.0 | 8.7 | 9.5 |
| 5-2 | C | 10.0 | 10.0 | 10.0 | 15.0 | 15.0 | 20.0 |
| 5-3 | C | 8.0 | 9.5 | 9.5 | 8.7 | 10.0 | 10.0 |
| 5-4 | C | 0* | 0* | 0* | 0* | 0* | 0* |
| 5-5 | C | 6.7 | 6.7 | 9.5 | 6.7 | 7.5 | 10.0 |
| 5-6 | C | 9.5 | 9.5 | 9.5 | 10.0 | 10.0 | 10.0 |
| 6 | C | 9.5 | 10.0 | 10.0 | 10.0 | 15.0 | 15.0 |
| 7-1 | B | 0.2 | 0.2 | 0.5 | 10.0 | 10.0 | 10.0 |
| 7-2 | B | 0.2 | 0.2 | 0.5 | 10.0 | 10.0 | 10.0 |

Table 4

Results of Tests of Emulsification of 2-Heptylundecyl Isostearate

| Invention Emulsifiers | (I) | Composition Proportion (wt.%) (II) | (III) | (IV) | HLB | Emulsion Type |
|---|---|---|---|---|---|---|
| 1-1 | 73.5 | 0.72 | 4.8 | 20.98 | 8.2 | O/W |
| 1-2 | 85.0 | 0.65 | 4.5 | 9.85 | 9.2 | O/W |
| 1-3 | 72.0 | 0.90 | 3.7 | 23.40 | 10.6 | O/W |
| 1-4 | 70.0 | 0.70 | 4.2 | 25.10 | 10.3 | O/W |
| 1-5 | 60.5 | 0.92 | 4.4 | 34.18 | 11.6 | O/W |
| 1-6 | 75.0 | 0.58 | 3.7 | 20.72 | 13.2 | O/W |
| Comparative | | | | | | |

Table 4-continued

Results of Tests of Emulsification of 2-Heptylundecyl Isostearate

| Invention Emulsifiers | Composition Proportion (wt.%) | | | | HLB | Emulsion Type |
|---|---|---|---|---|---|---|
| | (I) | (II) | (III) | (IV) | | |
| Emulsifiers | | | | | | |
| 2-1 | 70.0 | 0 | 5.0 | 25.0 | 10.3 | O/W |
| 2-2 | 69.8 | 0.2 | 0 | 30.0 | 10.3 | O/W |
| 2-3 | 72.0 | 0.2 | 1.4 | 26.4 | 10.3 | O/W |
| 2-4 | 40.2 | 0.6 | 4.2 | 55.0 | 10.1 | O/W |
| 2-5 | 20.0 | 0.6 | 2.4 | 77.0 | 10.0 | O/W |
| 2-6 | 100.0 | 0 | 0 | 0 | 10.4 | O/W |
| 2-7 | 0 | 0 | 0 | 100 | 9.9 | O/W |
| 2-8 | 0 | 0 | 100 | 0 | — | O/W |
| 3-1 | POE (20) sorbitan monooleate/sorbitan monooleate | | | | 8.0 | O/W |
| 3-2 | | | | | 9.0 | O/W |
| 3-3 | | | | | 10.0 | O/W |
| 3-4 | | | | | 11.0 | O/W |
| 3-5 | | | | | 12.0 | O/W |
| 3-6 | | | | | 13.0 | O/W |
| 3-7 | POE (20) sorbitan trioleate | | | | 11.0 | O/W |
| 4-1 | POE (8) stearate/glycerol monostearate | | | | 8.0 | O/W |
| 4-2 | | | | | 9.0 | O/W |
| 4-3 | | | | | 10.0 | O/W |
| 4-4 | | | | | 11.0 | O/W |
| 4-5 | POE (50) stearate/glycerol monostearate | | | | 12.0 | O/W |
| 4-6 | '' | | | | 13.0 | O/W |
| 5-1 | POE (5) oleyl ether | | | | 8.8 | O/W |
| 5-2 | POE (5) nonylphenyl ether | | | | 9.2 | O/W |
| 5-3 | POE (6) oleyl ether | | | | 10.0 | O/W |
| 5-4 | POE (6) stearyl ether | | | | 9.4 | O/W |
| 5-5 | POE (7) cetyl ether | | | | 10.7 | O/W |
| 5-6 | POE (9) oleyl ether | | | | 12.1 | O/W |
| 6 | polyoxyethylene-polyoxypropylene | | | | — | O/W |
| 7-1 | sodium oleate | | | | — | O/W |
| 7-2 | potassium oleate | | | | — | O/W |

| Invention Emulsifiers | Emulsifiability | Stability of Formed Emulsion | | | | | |
|---|---|---|---|---|---|---|---|
| | | after one day's standing | | | after one week's standing | | |
| | | 5°C | 20°C | 40°C | 5°C | 20°C | 40°C |
| 1-1 | B | 0 | 0 | 0 | 0.2 | 0.3 | 0.5 |
| 1-2 | A | 0 | 0 | 0 | 0 | 0 | 0 |
| 1-3 | A | 0 | 0 | 0 | 0 | 0 | 0 |
| 1-4 | A | 0 | 0 | 0 | 0 | 0 | 0 |
| 1-5 | A | 0 | 0 | 0 | 0 | 0 | 0 |
| 1-6 | B | 0 | 0 | 0 | 0 | 0 | 0 |
| Comparative Emulsifiers | | | | | | | |
| 2-1 | C | 3.5 | 4.7 | 5.5 | 6.7 | 9.3 | 9.3 |
| 2-2 | C | 4.5 | 5.0 | 6.0 | 8.5 | 8.0 | 8.5 |
| 2-3 | B | 0.2 | 0.2 | 0.3 | 8.7 | 8.7 | 9.3 |
| 2-4 | B | 2.2 | 2.5 | 2.0 | 8.7 | 9.0 | 9.3 |
| 2-5 | C | 8.3 | 8.3 | 8.7 | 10.0 | 10.2 | 15.0 |
| 2-6 | C | 8.7 | 9.0 | 9.3 | 10.0 | 10.0 | 10.0 |
| 2-7 | C | 12.5 | 12.5 | 14.0 | 13.8 | 14.2 | 15.0 |
| 2-8 | C | 20.0 | 20.0 | 20.0 | 20.0 | 20.0 | 20.0 |
| 3-1 | C | 0* | 0* | 0* | 0* | 0* | 0.1 |
| 3-2 | B | 0 | 0 | 0 | 0.1 | 0.1 | 0.6 |
| 3-3 | A | 0 | 0 | 0 | 0.2 | 0.2 | 0.6 |
| 3-4 | C | 0 | 0 | 0 | 8.9 | 8.9 | 9.3 |
| 3-5 | C | 8.7 | 9.9 | 10.4 | 10.4 | 10.4 | 10.7 |
| 3-6 | C | 8.9 | 8.9 | 8.9 | 10.4 | 10.7 | 10.7 |
| 3-7 | C | 0 | 0 | 0 | 0.2 | 0.6 | 0.7 |
| 4-1 | C | 0* | 0* | 0* | 0* | 0* | 0* |
| 4-2 | C | 0* | 0* | 0*. | 0* | 0* | 0* |
| 4-3 | C | 0* | 0* | 0* | 0* | 0* | 0* |
| 4-4 | C | 0* | 0* | 0* | 0* | 0.7 | 2.1 |
| 4-5 | C | 0* | 0* | 0* | 1.1 | 2.1 | 1.1 |
| 4-6 | C | 0* | 0* | 0* | 4.7 | 5.4 | 8.1 |
| 5-1 | C | 8.1 | 9.5 | 9.7 | 9.7 | 9.5 | 9.7 |
| 5-2 | C | 8.7 | 12.5 | 13.5 | 14.5 | 14.5 | 15.0 |
| 5-3 | C | 0 | 0 | 0 | 4.5 | 5.4 | 9.1 |
| 5-4 | C | 0 | 0 | 0 | 8.7 | 9.3 | 9.3 |
| 5-5 | C | 6.7 | 8.0 | 8.7 | 6.7 | 8.1 | 8.9 |
| 5-6 | C | 7.3 | 9.1 | 10.0 | 7.3 | 9.3 | 10.1 |
| 6 | C | 10.0 | 12.5 | 14.5 | 17.0 | 17.5 | 17.5 |
| 7-1 | C | 6.2 | 4.0 | 10.0 | 9.3 | 8.0 | 12.5 |
| 7-2 | C | 5.7 | 4.2 | 10.0 | 9.7 | 8.5 | 12.5 |

Table 5

Results of Tests of Emulsification of Glycerol Tris-2-ethyl-hexanoate

| Invention Emulsifiers | Composition Proportion (wt.%) | | | | HLB | Emulsion Type |
|---|---|---|---|---|---|---|
| | (I) | (II) | (III) | (IV) | | |
| 1-1 | 73.5 | 0.72 | 4.8 | 20.98 | 8.2 | O/W |
| 1-2 | 85.0 | 0.65 | 4.5 | 9.85 | 9.2 | O/W |
| 1-3 | 72.0 | 0.90 | 3.7 | 23.40 | 10.6 | O/W |
| 1-4 | 70.0 | 0.70 | 4.2 | 25.10 | 10.3 | O/W |
| 1-5 | 60.5 | 0.92 | 4.4 | 34.18 | 11.6 | O/W |
| 1-6 | 75.0 | 0.58 | 3.7 | 20.72 | 13.2 | O/W |
| Comparative Emulsifiers | | | | | | |
| 2-1 | 70.0 | 0 | 5.0 | 25.0 | 10.3 | O/W |
| 2-2 | 69.8 | 0.2 | 0 | 30.0 | 10.3 | O/W |
| 2-3 | 72.0 | 0.2 | 1.4 | 26.4 | 10.3 | O/W |
| 2-4 | 4.2 | 0.6 | 4.2 | 55.0 | 10.1 | O/W |
| 2-5 | 20.0 | 0.6 | 2.4 | 77.0 | 10.0 | O/W |
| 2-6 | 100.0 | 0 | 0 | 0 | 10.4 | O/W |
| 2-7 | 0 | 0 | 0 | 100 | 9.9 | O/W |
| 2-8 | 0 | 0 | 100 | 0 | — | O/W |
| 3-1 | POE (20) sorbitan monooleate/sorbitan monooleate | | | | 8.0 | O/W |
| 3-2 | | | | | 9.0 | O/W |
| 3-3 | | | | | 10.0 | O/W |
| 3-4 | | | | | 11.0 | O/W |
| 3-5 | | | | | 12.0 | O/W |
| 3-6 | | | | | 13.0 | O/W |
| 3-7 | POE (20) sorbitan trioleate | | | | 11.0 | O/W |
| 4-1 | POE (8) stearate/glycerol monostearate | | | | 8.0 | O/W |
| 4-2 | | | | | 9.0 | O/W |
| 4-3 | | | | | 10.0 | O/W |
| 4-4 | | | | | 11.0 | O/W |
| 4-5 | POE (50) stearate/glycerol monostearate | | | | 12.0 | O/W |
| 4-6 | ″ | | | | 13.0 | O/W |
| 5-1 | POE (5) oleyl ether | | | | 8.8 | O/W |
| 5-2 | POE (5) nonylphenyl ether | | | | 9.2 | O/W |
| 5-3 | POE (6) oleyl ether | | | | 10.0 | O/W |
| 5-4 | POE (6) stearyl ether | | | | 9.4 | O/W |
| 5-5 | POE (7) cetyl ether | | | | 10.7 | O/W |
| 5-6 | POE (9) oleyl ether | | | | 12.1 | O/W |
| 6 | polyoxyethylene-polyoxypropylene condensate | | | | — | O/W |
| 7-1 | sodium oleate | | | | — | O/W |
| 7-2 | potassium oleate | | | | — | O/W |

| Invention Emulsifiers | Emulsifiability | Stability of Formed Emulsion | | | | | |
|---|---|---|---|---|---|---|---|
| | | after one day's standing | | | after one week's standing | | |
| | | 5°C | 20°C | 40°C | 5°C | 20°C | 40°C |
| 1-1 | A | 0 | 0 | 0 | 0 | 0 | 0 |
| 1-2 | A | 0 | 0 | 0 | 0 | 0 | 0 |
| 1-3 | A | 0 | 0 | 0 | 0 | 0 | 0 |
| 1-4 | A | 0 | 0 | 0 | 0 | 0 | 0 |
| 1-5 | A | 0 | 0 | 0 | 0 | 0 | 0 |
| 1-6 | A | 0 | 0 | 0 | 0 | 0.2 | 2.1 |
| Comparative Emulsifiers | | | | | | | |
| 2-1 | C | 4.5 | 4.7 | 4.7 | 8.5 | 9.2 | 9.5 |
| 2-2 | C | 4.5 | 4.9 | 5.3 | 8.0 | 9.7 | 10.0 |
| 2-3 | B | 0.2 | 0.2 | 0.2 | 0.8 | 1.0 | 1.0 |
| 2-4 | C | 8.0 | 8.7 | 8.9 | 9.3 | 9.3 | 9.5 |
| 2-5 | C | 9.3 | 9.5 | 9.5 | 9.7 | 10.0 | 12.0 |
| 2-6 | C | 7.7 | 8.0 | 8.7 | 8.7 | 9.3 | 10.0 |
| 2-7 | C | 8.7 | 9.5 | 12.5 | 12.5 | 14.7 | 15.0 |
| 2-8 | C | 20.0 | 20.0 | 20.0 | 20.0 | 20.0 | 20.0 |
| 3-1 | A | 0 | 0 | 0 | 0.2 | 0.2 | 0.2 |
| 3-2 | B | 0 | 0 | 0 | 0.2 | 0.2 | 0.2 |
| 3-3 | C | 0 | 0 | 0 | 0.2 | 0.2 | 0.2 |
| 3-4 | C | 0 | 0 | 0 | 0.2 | 5.4 | 10.0 |
| 3-5 | C | 0 | 0 | 8.5 | 9.7 | 9.6 | 9.3 |
| 3-6 | C | 0 | 2.5 | 8.5 | 8.4 | 9.3 | 8.9 |
| 3-7 | C | 0 | 9.7 | 9.7 | 9.3 | 9.7 | 10.0 |
| 4-1 | C | 0* | 0* | 0* | 0* | 0* | 0* |
| 4-2 | C | 0* | 0* | 0* | 0* | 0* | 0* |
| 4-3 | C | 0* | 0* | 0* | 0* | 0* | 0* |
| 4-4 | C | 0* | 8.5 | 9.5 | 0* | 8.7 | 9.3 |
| 4-5 | C | 0* | 8.5 | 9.5 | 0* | 8.7 | 9.7 |
| 4-6 | C | 0* | 8.5 | 8.5 | 0* | 10.0 | 9.6 |
| 5-1 | C | 8.7 | 9.5 | 9.7 | 8.7 | 10.0 | 10.0 |
| 5-2 | C | 12.5 | 13.5 | 12.0 | 14.3 | 20.0 | 20.0 |
| 5-3 | C | 6.7 | 8.0 | 6.7 | 6.0 | 8.3 | 7.3 |
| 5-4 | C | 0* | 0* | 0* | 0.8 | 1.0 | 2.5 |
| 5-5 | C | 6.7 | 8.3 | 9.0 | 6.7 | 8.3 | 9.6 |
| 5-6 | C | 0 | 0 | 0 | 2.0 | 2.0 | 2.7 |
| 6 | C | 10.0 | 10.5 | 12.0 | 10.0 | 10.5 | 12.0 |
| 7-1 | B | 0 | 0.2 | 0.2 | 0.4 | 2.0 | 2.1 |
| 7-2 | B | 0 | 0.2 | 0.2 | 0.4 | 2.0 | 2.7 |

As is seen from the results obtained in Examples 2 to 5, although vegetable oils or synthetic ester oils cannot be emulsified at all or can be emulsified only insufficiently by conventional known emulsifiers, they can easily be emulsified by the emulsifying agent composition of this invention and good emulsions having an excellent stability can be obtained. It is also seen that even if the same components as in this invention are used, if the proportion of these components is outside the ranges specified in this invention, no satisfactory emulsifying effect can be attained and the stability of the resulting emulsion is poor.

EXAMPLE 6

(O/W Cream)

An emulsifying agent composition comprising the following components was prepared:

| | | |
|---|---|---|
| (I) | polyoxyethylene ($\bar{P}$=10) sorbitol oleate (average degree of esterification = 3.0) | 73.5% |
| (II) | sodium oleate | 0.72% |
| (III) | oleic acid | 4.8% |
| (IV) | polyethylene glycol oleate (average molecular weight = 200) | 20.98% |

This emulsifying agent composition was a yellowish brown liquid having a specific gravity ($d_4^{20}$) of 0.962, a viscosity of 172 cps as measured at 20°C, a saponification value of 118.8 and an HLB value of 8.2.

by using this emulsifying agent composition, an O/W type cream having the following composition was prepared:

| | | |
|---|---|---|
| (1) | camellia oil | 25 parts |
| | bees wax | 5 parts |
| | paraffin wax | 5 parts |
| | vaseline | 7 parts |
| | emulsifying agent composition | 6 parts |
| (2) | glycerin | 5 parts |
| | water | 47 parts |
| (3) | perfume, preservative | suitable amounts |

Components (1) and components (2) were separately heated and melted, and both the melts were mixed under vigorous agitation to form an emulsion. While the emulsion was being cooled, components (3) were added and dispersed uniformly to obtain a cream. This cream had a very good emulsion state.

EXAMPLE 7

(Milky Lotion)

An emulsifying agent having the following components was prepared:

| | | |
|---|---|---|
| (I) | polyoxyethylene ($\bar{P}$=40) sorbitol oleate (average degree of esterification = 4.5) | 60.5% |
| (II) | sodium oleate | 0.92% |
| (III) | oleic acid | 4.4% |
| (IV) | polyethylene glycol oleate (average molecular weight = 800) | 34.18% |

This emulsifying agent composition was a yellowish brown liquid having a specific gravity ($d_4^{20}$) of 1.03, a viscosity of 321 cop as measured at 20°C, a saponification value of 82.8 and an HLB value of 11.6.

By using this emulsifying agent composition, a milky lotion having the following composition was prepared in the same manner as described in Example 6.

| | | |
|---|---|---|
| (1) | olive oil | 30 parts |
| | bees wax | 2 parts |
| | paraffin wax | 2 parts |
| | cetyl alcohol | 1 part |
| | emulsifying agent composition | 5 parts |
| (2) | glycerin | 5 parts |
| | water | 55 parts |
| (3) | perfume, preservatives | |

The resulting milky lotion had a good emulsion state, and was very stable even after passage of a long time.

The embodiments of the invention in which an exclusive property or privilege is claimed are defined as follows:

1. An emulsifying or solubilizing composition, consisting essentially of
   I. from 58 to 95 percent by weight of a surface active agent having the formula

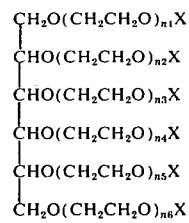

wherein the sum of $n1$ to $n6$ is from 10 to 60 and, on the average, up to 3 of the X's are hydrogen and the balance of the X's are linear unsaturated acyl groups having 18 carbon atoms, II. from 0.5 to 1.0 percent by weight of an alkali metal salt of a linear fatty acid having 12 to 18 carbon atoms,
   III. from 2.5 to 6.0 percent by weight of a linear fatty acid having 12 to 18 carbon atoms, and
   IV. from 2 to 35 percent by weight of a $C_{18}$ linear unsaturated fatty acid ester of polyethylene glycol having an average molecular weight of 150 to 2000.

2. A composition as claimed in claim 1 in which ingredient II is sodium oleate and ingredient III is oleic acid.

3. A composition as claimed in claim 1 in which ingredient II is sodium laurate and ingredient III is lauric acid.

4. A composition as claimed in claim 1 in which ingredient II is sodium laurate and ingredient III is myristic acid.

5. A composition as claimed in claim 1 in which ingredient II is sodium myristate and ingredient III is myristic acid.

6. A composition as claimed in claim 1, containing from about 60 to 80 percent by weight of ingredient I.

7. An oil-in-water emulsion containing as an emulsifier for the oil phase, from 5 to 100 percent by weight, based on the weight of the oil components, of a composition as claimed in claim 1.

8. An emulsion as claimed in claim 7, in which said oil component consists of a liquid vegetable oil consisting essentially of triglycides containing several unsaturated aliphatic hydrocarbon groups or synthetic ester oils having at least one branched alkyl group obtained by reacting a branched or linear higher fatty acid with a branched or linear higher alcohol.

9. An emulsion as claimed in claim 7 in which the oil component is selected from the group consisting of camellia oil, olive oil, safflower oil, rapeseed oil, palm oil and cotton seed oil.

10. An emulsion as claimed in claim 7 in which the oil component is selected from the group consisting of 2-heptylundecyl isostearate, glycerol-tris-2-ethylhexanoate, hexadecyl-2-ethylhexanoate, hexadecyl isostearate and hexadecyl isotridecanoate.

* * * * *